(12) United States Patent
Jönsson

(10) Patent No.: US 7,886,753 B2
(45) Date of Patent: Feb. 15, 2011

(54) DISINFECTION APPARATUS WITH PUMP DEVICE

(75) Inventor: Christer Jönsson, Växjö (SE)

(73) Assignee: Getinge Disinfection AB, Vaxjo (SE)

( * ) Notice: Subject to any disclaimer, the term of this patent is extended or adjusted under 35 U.S.C. 154(b) by 412 days.

(21) Appl. No.: 11/587,035

(22) PCT Filed: Apr. 26, 2005

(86) PCT No.: PCT/SE2005/000603

§ 371 (c)(1),
(2), (4) Date: Jul. 31, 2007

(87) PCT Pub. No.: WO2005/102399

PCT Pub. Date: Nov. 3, 2005

(65) Prior Publication Data

US 2007/0277860 A1    Dec. 6, 2007

(30) Foreign Application Priority Data

Apr. 27, 2004    (SE) .................................... 0401073

(51) Int. Cl.
*B08B 6/00* (2006.01)
(52) U.S. Cl. ................... 134/184; 134/56 D; 134/57 D; 134/58 D; 134/201
(58) Field of Classification Search .................. None
See application file for complete search history.

(56) References Cited

U.S. PATENT DOCUMENTS

| | | | |
|---|---|---|---|
| 3,754,738 A * | 8/1973 | Blazer et al. ................... 261/30 |
| 4,678,404 A * | 7/1987 | Lorett et al. ................... 417/45 |
| 5,225,160 A | 7/1993 | Sanford et al. | |
| 5,331,986 A * | 7/1994 | Lim et al. ..................... 134/88 |
| 6,013,227 A | 1/2000 | Lin et al. | |
| 6,423,266 B1 | 7/2002 | Choperena et al. | |
| 6,454,872 B1 * | 9/2002 | Miller et al. ................... 134/10 |
| 6,482,358 B1 | 11/2002 | Kelsch et al. | |
| 6,555,054 B1 | 4/2003 | Kral et al. | |

(Continued)

FOREIGN PATENT DOCUMENTS

DE    3937023 A1    5/1991

(Continued)

OTHER PUBLICATIONS

Abstract of JP 2003-521345, published Jul. 15, 2003.

*Primary Examiner*—Michael Barr
*Assistant Examiner*—Jason Y Ko
(74) *Attorney, Agent, or Firm*—Harness, Dickey & Pierce, P.L.C.

(57) ABSTRACT

The invention relates to a disinfection apparatus (1) for disinfecting liquid cleaning of health care objects and the like, which disinfection equipment comprises a washing system (2) for supplying liquid to a chamber (3) which is adapted to hold said objects in cleaning, a pump (4) for pumping liquid in said washing system (2), and at least one collection space (5) connected to the inlet (6) of the pump for collecting liquid from said chamber (3) to the pump (4). Said collection space (5) is defined by at least one partition (7) which has an extent horizontally from the inlet (6) of the pump and which screens the inlet (6) of the pump from liquid descending into the chamber (3) at least nearest the inlet (6) of the pump.

12 Claims, 3 Drawing Sheets

U.S. PATENT DOCUMENTS

| | | |
|---|---|---|
| 6,582,654 B1 | 6/2003 | Kral et al. |
| 2003/0190257 A1 | 10/2003 | Halstead et al. |
| 2004/0250837 A1* | 12/2004 | Watson et al. .............. 134/25.2 |

FOREIGN PATENT DOCUMENTS

| | | |
|---|---|---|
| JP | 4-54933 | 2/1992 |
| JP | 11-277005 | 10/1999 |
| WO | WO 99/30748 | 6/1999 |
| WO | WO 01/56615 | 8/2001 |

* cited by examiner

DISINFECTION APPARATUS WITH PUMP DEVICE

FIELD OF THE INVENTION

The present invention relates to a disinfection apparatus for disinfecting liquid cleaning of health care objects and the like, which disinfection apparatus comprises a washing system for supplying liquid to a chamber which is adapted to hold said objects in cleaning, a pump means for pumping liquid in said washing system, at least one collection space connected to the inlet of the pump for collecting liquid from said chamber to the pump.

BACKGROUND ART

Disinfection apparatus of the above type are well known and are also called washer disinfectors. They are used for cleaning and disinfection of goods, instruments and other objects that are used in, for instance, hospitals, laboratories and in the pharmaceutical industry. In these fields disinfection is an important activity, for instance, to prevent the spread of infection and bacterial growth. As examples of objects that need be disinfected, mention can be made of vessels, instrument containers, hospital beds, trolleys, wheelchairs, animal cages, machine parts for health care applications and other bulky objects.

One type of disinfection apparatus is provided with what is referred to as walk-in chambers, which are large enough for an individual to enter and/or large enough for a trolley/cart or other equipment to be inserted.

Washer disinfectors of this kind usually have a disinfection chamber into which a plurality of nozzles open. The nozzles are connected via, for instance, a high-pressure pump to a separate liquid tank. The disinfection chamber usually has a liquid-permeable chamber floor mounted over the bottom of the chamber, on which chamber floor objects are placed to be cleaned. In liquid cleaning of objects in the chamber, the descending liquid is collected at the bottom of the chamber, and the liquid flows to a second pump, which is sometimes also referred to as a sump pump, which makes it possible to pump the liquid out of the liquid system, or alternatively return the liquid to the liquid system.

Disinfectors of this type are usually installed in a chamber cavity, which is also referred to as a pit, in the installation floor so that the liquid-permeable chamber floor and the surrounding floor outside the entrance to the chamber are positioned at the same level. In this case, it is desirable to reduce said cavity in the floor without deteriorating the intended function of the wash disinfector.

Alternatively, the washer disinfector can be installed as a separate unit directly on the floor with an adjusted and associated ramp in front of the entrance to the chamber to allow objects, for instance on trolleys, to be moved into and out of the chamber. For reasons of comfort for instance, it is desirable that said ramp be as low as possible.

In both cases, it is thus desirable to reduce the so-called installation height, i.e. the difference in height between the liquid-permeable chamber floor and the bottom of the chamber. However, the sump pump limits the possibilities of reducing the installation height since at low liquid levels it tends to at least partly draw in air, thereby deteriorating the intended function of the pump.

Several solutions have been tested to solve the above problems. For instance, in addition to said cavity, a further recess (ascending pipe) has been arranged at the inlet of the pump to collect a liquid column in order to ensure that the sump pump obtains sufficient liquid and, thus, reduce the risk of the sump pump drawing in air. However, the drawback is that not all installation floors allow such deep recesses, for instance for reasons of construction. It is also advantageous to be able to replace an old disinfection apparatus with a new one without the floor below having to be greatly modified, as described above.

Washer disinfectors further usually have a process step, in which the liquid is heated before being supplied to the chamber. To allow quick heating and to obtain a quick cleaning step, it is desirable to have a small but sufficient liquid volume in the system. Thus, there is a need to reduce the use of liquid tanks and at the same time have a sufficient volume in the system, so that on the one hand the required cleanness is achieved and, on the other, the sump pump works according to its intended function. Moreover it is desirable to be able to reduce the number of machine components of the disinfection apparatus and yet maintain its desired disinfection function.

Finally it is advantageous to provide a robust, cost-effective and reliable high quality disinfection apparatus.

SUMMARY OF THE INVENTION

The object of the present invention is to provide a disinfection apparatus which allows improvements in relation to prior-art disinfection apparatus in one or more of the above aspects.

The object is achieved by a disinfection apparatus of the type mentioned by way of introduction, which is further characterised in that said collection space is defined by at least one partition which has an extent horizontally from the inlet of the pump and which screens the inlet of the pump from liquid descending into the chamber at least nearest the inlet of the pump.

The present invention as defined in claim 1 gives several advantages, such as reducing said installation height and avoiding the need to use these deep recesses.

Moreover the disinfection apparatus according to the invention makes it possible to refrain from using separate liquid tanks for returning liquid in the liquid system. It will also be possible to use only one pump means in the washing system, for instance for circulating the liquid.

The partition thus restrains the supply of air in an at least partial liquid presence in the collection space, whereby the supply of liquid occurs at the partition spaced from the inlet of the pump.

By the expression the partition "screens" the inlet of the pump is meant to prevent, restrain or divide so as to promote the intended liquid supply of the disinfection apparatus in the liquid system.

The partition preferably has a substantially horizontal extent from the inlet of the pump along at least parts of the bottom of the chamber, said partition extending at least partly along said collection space. The collection space can thus have a substantially horizontal extent in order to ensure that sufficient liquid can be collected at the pump inlet.

Said partition and the bottom of the chamber preferably form a peripheral flow gap, whose area exceeds the inlet area of the pump, which makes it possible to reduce the flow rate and ensure a good liquid collection at the inlet of the pump.

The highest point of the flow gap is preferably positioned at a lower level than the highest point of the pump inlet and the difference in height between the highest point of the flow gap and the cross-sectional dimension of the pump inlet in the vertical direction seen from below is preferably less than 75%, more preferred less than 60% and most advantageously less than 50%. This makes it possible to restrain the supply of air and the partition thus provides good screening nearest the inlet of the pump.

The partition can have an at least partially descending extent seen horizontally from the inlet of the pump, and said descending extent of the partition can be arranged at least nearest the periphery of the partition. The descending extent results not only in the air-restraining function but also in the fact that the flow gap of the collection space can increase inside the periphery of the partition, which in turn improves the possibility of holding liquid.

The partition is advantageously a cap-shaped means with a downward cavity. The liquid descending in the chamber can thus flow off along the upper portions of the cap-shaped means and can quietly flow at an adjusted flow rate to the collection space so as to allow a safe supply of liquid to the inlet of the pump.

The downward cavity can thus restrain the supply of air as long as the liquid level exceeds the supply passages of the cavity. The part of an upper space in the downward cavity which is not occupied by liquid can thus at least initially contain air, but the cap-shaped means can restrain the supply of air.

The cap-shaped means can thus form a collection space with a supply of liquid which can exceed the required flow of the pump inlet.

The collection space can, in addition to said partition, also be defined by at least one vertical partition so as to restrain the supply of air.

The pump means can be a centrifugal pump which has an inclination of its axis ($\alpha$) relative to the horizontal plane (A) which is smaller than 90 degrees, wherein said inclination of axis ($\alpha$) preferably is between 30° and 60°, more preferred between 35° and 55° and more advantageously between 40° and 50° and most advantageously about 45°.

This makes it possible to provide a good liquid flow to the pump and its inlet, thus making it possible to reduce the installation height. The centrifugal pump also makes it possible to build up the required liquid pressure in the liquid system downstream of the pump.

BRIEF DESCRIPTION OF THE DRAWINGS

The invention will in the following be described with reference to the accompanying drawings, which for the purpose of exemplification illustrate preferred embodiments of the invention.

DESCRIPTION OF PREFERRED EMBODIMENTS

Figure 1:
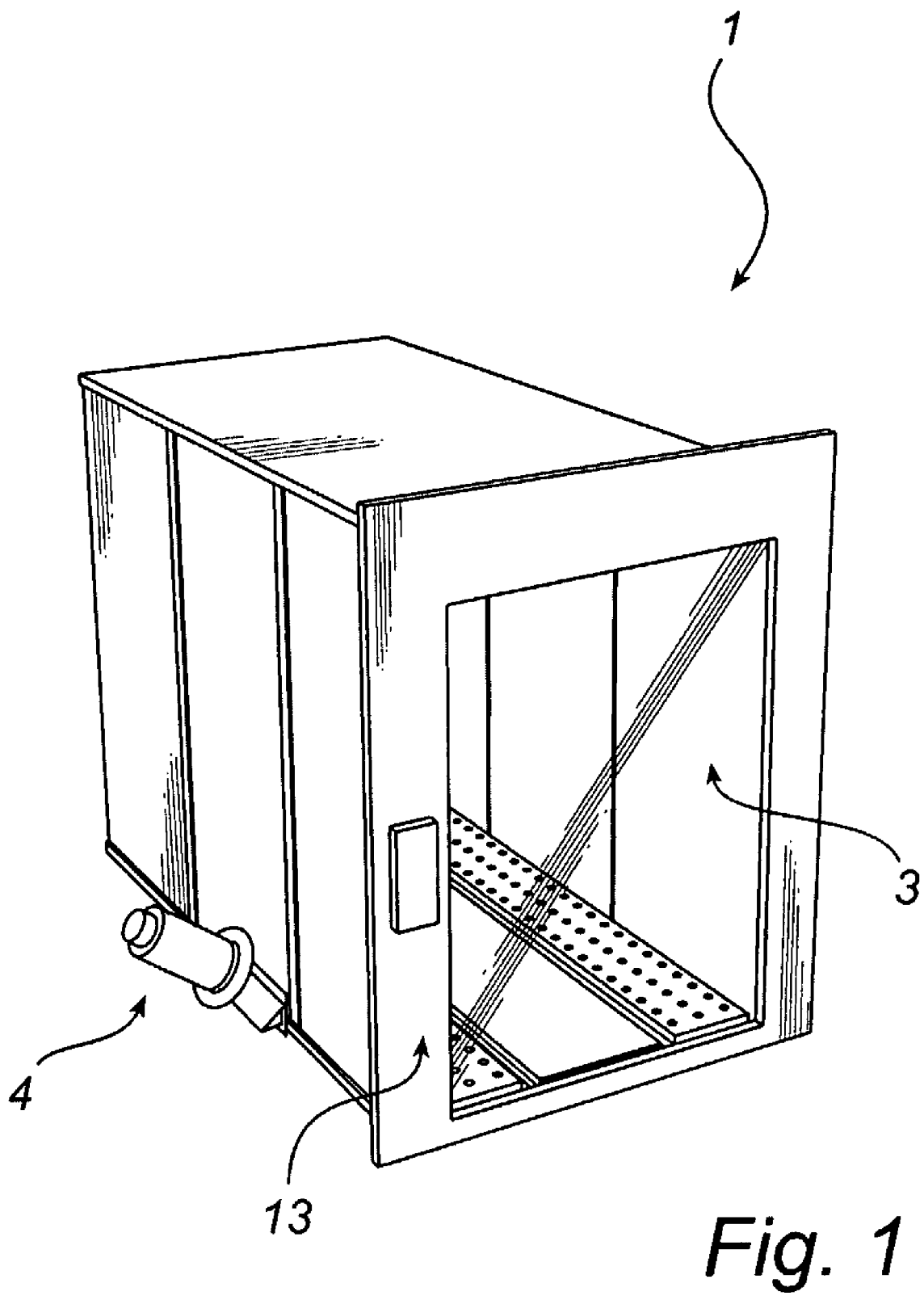
FIG. 1 is a schematic view of a disinfection apparatus according to a first embodiment of the invention.

FIG. 1 illustrates a disinfection apparatus 1 according to a first embodiment of the invention, which has a chamber 3 which is adapted to receive objects for disinfection. The chamber 3 is partly made from mountable wall, ceiling and floor elements of, for instance, stainless sheet steel. Moreover a movably arranged door 13 is mounted for opening and closing the entrance to the chamber.

Figure 2:
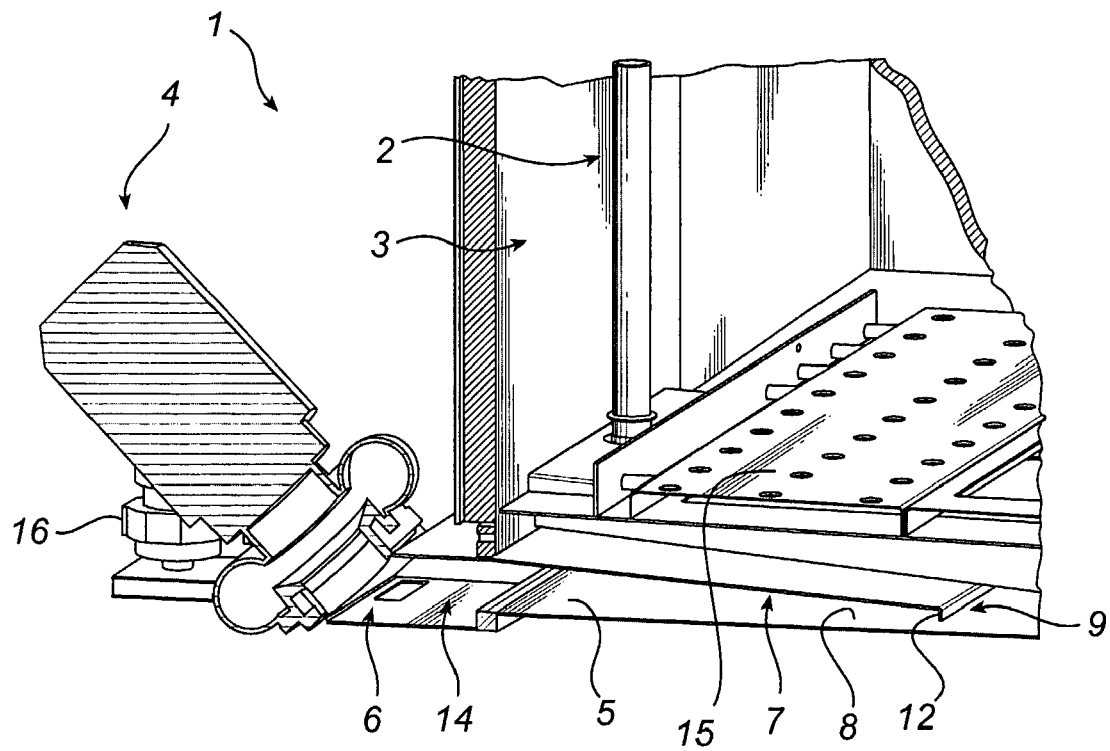
FIG. 2 shows in more detail parts of the disinfection apparatus in FIG. 1, partly in section, seen obliquely from the front.

FIG. 2 is, inter alia, a section of parts of the chamber of the disinfection apparatus 1. The disinfection apparatus 1 also has a centrifugal pump 4, which via an inlet 6 is connected to a collection space 5 which extends substantially horizontally. The collection space 5 is in this case formed of an elongated sump 14 and a space between a cap-shaped means 7 (also called partition) and the bottom 8 of the chamber. The cap-shaped means 7 is connected to the inlet 6 of the pump and extends substantially horizontally through the chamber wall and along parts of the bottom 8 of the chamber where the cap-shaped means has a slightly inclined extent. A peripheral flow gap 9 is thus formed along the periphery of the cap-shaped means 7 in the chamber 3 and the bottom 8 of the chamber to provide the required liquid supply to the pump 4. The pump 4 is further connected to a washing system 2 which is shown in FIG. 2 in the form of a washing pipe which, for instance, is provided with nozzles (not shown) for distributing liquid in the chamber 3. FIG. 2 also shows a liquid-permeable floor 15 which is spaced from the bottom 8 of the chamber and suitably arranged at the same level as the floor (not shown) outside the entrance to the chamber. The liquid-permeable floor 15 serves to carry, for instance, the objects that are placed in the chamber for disinfection, such as trolleys carrying objects.

Figure 3:
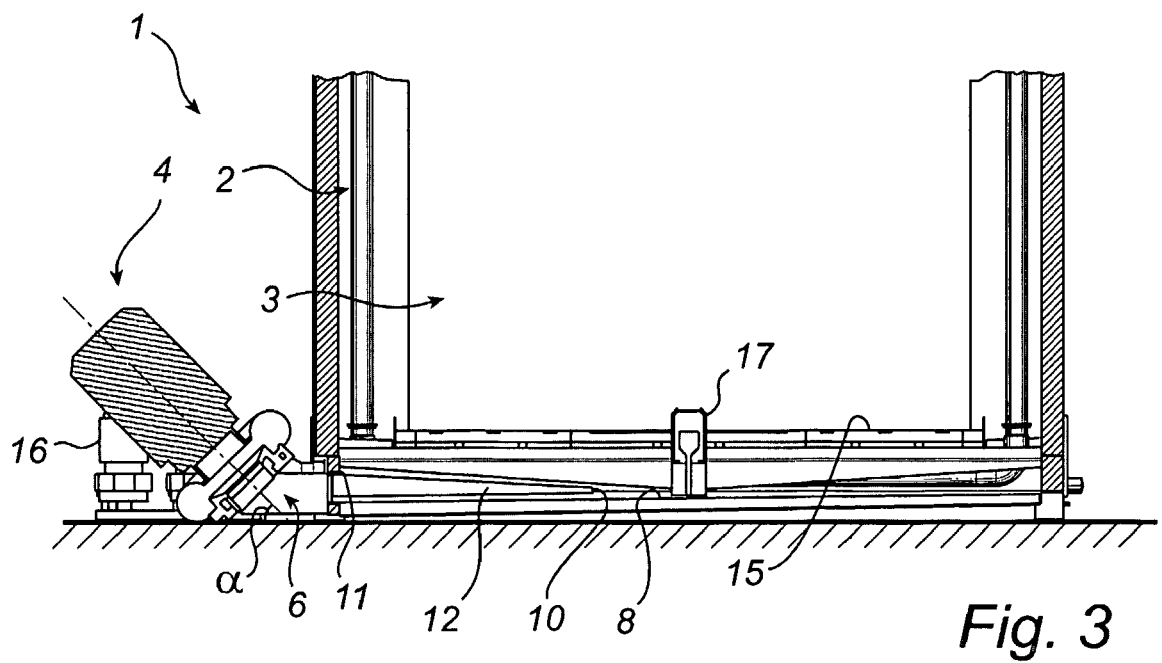
FIG. 3 is a section of the disinfection apparatus in FIG. 1, seen from the front.

FIG. 3 shows that the bottom 8 of the chamber has an extent which is inclined to the horizontal plane, the inclination being adjusted to allow used liquid in the chamber 3 to flow to the inlet 6 of the pump. The centrifugal pump 4 is angled relative to the horizontal plane with an inclination of the axis $\alpha$, which in this case is about 45°. This allows the space to be effectively used in the vertical direction at the pump inlet 6 compared with the case where the inclination of the axis $\alpha$ is for instance 0°. Although it is conceivable to have an inclination of the axis of 90°, this may, however, cause flow problems at the pump inlet 6.

Referring once more to FIG. 2, a vertical partition 12 is shown, which in this case is part of the cap-shaped means 7. FIG. 3 shows a highest point 11 of the pump inlet and a highest point 10 of the peripheral flow gap 9. The highest point 10 of the flow gap is at a level which, at the point 11, is below half of the cross-sectional dimension of the pump inlet 6 seen from below.

A drain pump 16 is also to be seen in FIGS. 2 and 3, which is arranged perpendicular to the horizontal plane and which is connected to the sump 14 for discharging used liquid to a drain (not shown). In the centre of the floor 15 of the chamber in FIG. 3, for instance a connecting device 17 is arranged, which is connectable to, for example, a trolley provided with wash nozzles for supplementary cleaning.

In the following the function of the disinfection apparatus will be described. Liquid, such as water, is supplied from a supply means (not shown) in the upper part of the chamber 3 to the sump 14 or to the bottom 8 of the chamber. This liquid can be supplied, for instance, from a public water system and/or from a temporary receptacle (not shown) for reuse of liquid. The supply means can ensure supply of hot water, cold water and/or distilled water (desalinated water).

Optionally, the sump 14 is supplied also with a disinfection liquid or some other cleaning liquid in addition to other liquids, which may occur by means of a flexible tube pump (not shown).

Figure 4:
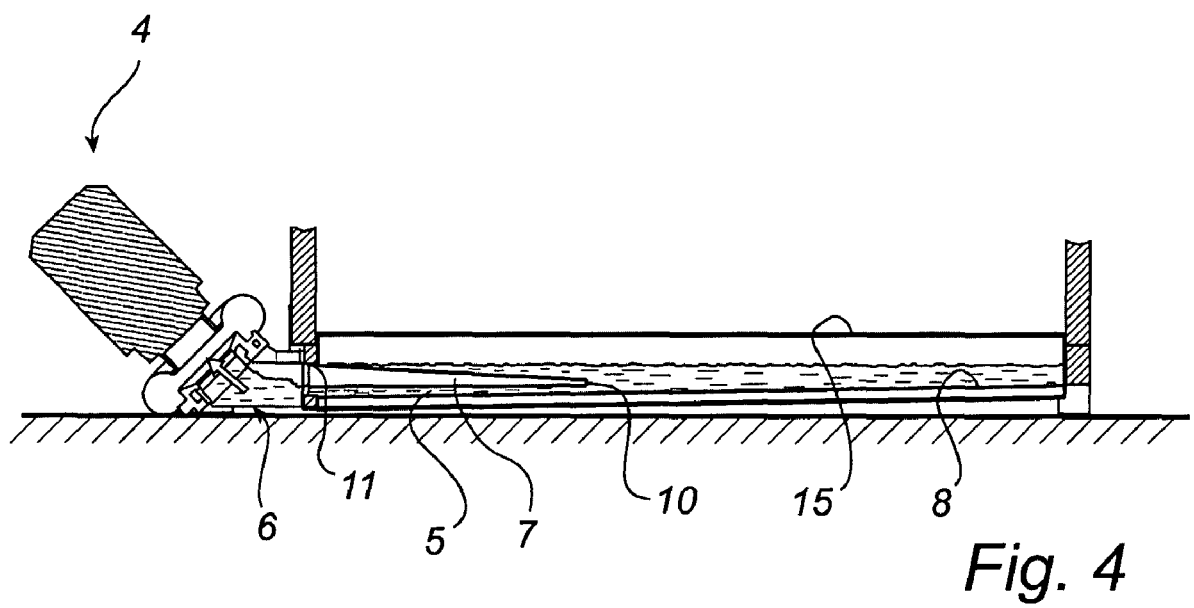
FIG. 4 is s section of the disinfection apparatus in FIG. 1, seen from the front, in an operative position.

As shown in FIG. 4, the liquid in the collection space 5 is drawn into the centrifugal pump 4 through the pump inlet 6. The pressurised liquid is then conducted to a heating device (not shown), which uses, for instance, heating by steam or the like. Then the pressurised liquid is filtered by a filtering means (not shown), after which the pressurised liquid is conducted to the washing system 2. In this case the washing system comprises, inter alia, two supply conduits, one for the left and one for the right side of the chamber 3, which conduct the liquid to, for instance, the plurality of washing pipes or alternatively movably arranged washing equipment or the like which are provided with said nozzles. The liquid is in this case pressurised from the centrifugal pump 4 out to the nozzles in the chamber and thus forms a pressurised liquid system. The liquid is ejected from the nozzles for the purpose of, for instance, disinfecting objects in the chamber 3.

The descending liquid flows through the liquid-permeable floor 15 and flows along the inclined floor 8 of the chamber. Liquid descending on the cap-shaped means 7 flows along the descending extent of the means down to the peripheral flow gap 9. Then the pump draws in the liquid in the collection space 5 so that it will be circulated once more. Thus, only one pump—the centrifugal pump 4—is required in order to circulate the liquid in this embodiment. The pressurised liquid system with the centrifugal pump 4 gives the advantage that the liquid can quickly be circulated and a possibility of eliminating the use of intermediate storage of the liquid. This means in turn that the liquid volume in the system can be reduced in contrast to prior-art systems which require intermediate storage of liquid.

In order to remove liquid from the circulation system, the drain pump 16 is used, which in turn can be connected to a cooling tank (not shown) for reducing the temperature of the liquid before drainage occurs to the drain. Parts of the liquid in the circulation system which can be reused are pumped by means of a tank pump (not shown) to the temporary receptacle.

The function of the cap-shaped means 7 thus is to restrain any supply of air to the centrifugal pump 4. Moreover, the adjusted design of the cap-shaped means 7 and the bottom 8 of the chamber makes it possible to reduce the risk of cavitation, and a substantially laminar supply of liquid can be provided adjacent to and around the collection space 5. In this embodiment, the area of the peripheral flow gap 9, around the cap-shaped means 7, exceeds the area of the pump inlet 6, thereby ensuring a sufficient supply of liquid.

Below follow various technical data for this embodiment. It should be noted, however, that these data merely illustrate examples and may therefore be varied by a person skilled in the art based on the inventive concept defined in the claims.

For instance, about 100 l of liquid, mainly consisting of water, are circulated in the liquid system. This amount of liquid can be compared with prior-art disinfection apparatus, which use intermediate storage of liquid and thus require a larger liquid volume in the liquid system, for instance about 300 l of liquid. To achieve the desired pressure and flow rate in the washing system 2, the centrifugal pump 4 must have good performance, in this case about 1300 l/min, which pump in operation pumps about 700 l/min. By comparison, the drain pump 16 has lower performance, for instance about 125 l/min, which drain pump in operation pumps about 100 l/min.

It will be appreciated that the above-described embodiment of the invention can be modified and varied by a person skilled in the art without departing from the inventive concept as defined in the claims. For instance, the cap-shaped means 7 can be formed of one or more partitions. The plurality of partitions can, for instance, form a labyrinth design of the bottom of the chamber so as to provide the desired supply of liquid to the inlet 6 of the pump. The cap-shaped means 7 can also extend between the partitions of the chamber, in which case the cap-shaped means 7 has a free end (on the opposite side of the pump inlet) in the chamber instead of three side portions of the embodiment. Moreover, one or more partitions can be movably controllable and adjustable, and can be adjusted, for instance, to the disinfection programme and other parameters. Furthermore the pump means 4 can be arranged at a distance from the sump (or an equivalent collection space) via the inlet 6. For example, the sump need not be arranged at the side of the chamber wall but adjacent the more central bottom portions. Moreover a plurality of different liquids can be used in addition to water, detergents, cleaning and disinfecting agents, which can have different pH values in the range 1.5-14.

The invention claimed is:

1. A disinfection apparatus for disinfecting liquid cleaning of objects to be cleaned, said disinfection apparatus comprising:
    a chamber adapted to receive said objects to be cleaned, said chamber having a bottom wall and side walls;
    a washing system for supplying liquid to said chamber;
    a pump for pumping liquid in said washing system; and
    at least one collecting region adjacent to an inlet of said pump for collecting liquid from said chamber to said pump, wherein:
    said pump is arranged outside said chamber and at least partly at a higher vertical level than said bottom wall of said chamber;
    said bottom wall of said chamber is inclined towards said inlet of said pump;
    said at least one collecting region is defined by said bottom wall of said chamber and at least one partition extending horizontally from at least one of the side walls in order to screen the inlet of said pump from liquid descending into said chamber at least nearest said inlet of the pump,
    said partition is arranged in such a way that a flow gap is formed between said partition and the bottom wall of the chamber along at least a portion of a periphery of said partition, and
    said partition is configured to direct liquid descending onto said partition towards said flow gap.

2. The disinfection apparatus as claimed in claim 1, wherein said flow gap has an area exceeding an inlet area of said pump.

3. The disinfection apparatus as claimed in claim 2, wherein a highest point of the flow gap is positioned at a lower level than a highest point of the pump inlet.

4. The disinfection apparatus as claimed in claim 1, wherein said at least one partition has a descending portion.

5. The disinfection apparatus as claimed in claim 4, wherein said descending portion of the at least one partition is arranged at least nearest to a periphery of the at least one partition.

6. The disinfection apparatus as claimed in claim 1, wherein said at least one collection region is defined by at least one vertical partition in addition to said at least one partition.

7. The disinfection apparatus as claimed in claim 1, wherein said pump is a centrifugal pump, arranged with an inclination relative to a horizontal plane which is smaller than 90 degrees.

8. The disinfection apparatus as claimed in claim 7, wherein said inclination is between 30° and 60°.

9. The disinfection apparatus as claimed in claim 8, wherein said inclination is between 35° and 55°.

10. The disinfection apparatus as claimed in claim 8, wherein said inclination is between 40° and 50°.

11. The disinfection apparatus as claimed in claim 10, wherein said inclination is about 45°.

12. A disinfection apparatus for disinfecting liquid cleaning of objects to be cleaned, said disinfection apparatus comprising:
- a chamber adapted to receive said objects to be cleaned, said chamber having a bottom wall and side walls;
- a washing system for supplying liquid to said chamber;
- a pump for pumping liquid in said washing system; and
- at least one collecting region adjacent to an inlet of said pump for collecting liquid from said chamber to said pump, wherein:
- said pump is arranged outside said chamber and at least partly at a higher vertical level than said bottom wall of said chamber;
- said bottom wall of said chamber is inclined towards said inlet of said pump;
- said at least one collecting region is defined by said bottom wall of said chamber and at least one partition extending horizontally from the inlet of said pump in order to screen the inlet of said pump from liquid descending into said chamber at least nearest said inlet of the pump,
- said partition is arranged in such a way that a flow gap is formed between said partition and the bottom wall of the chamber along at least a portion of a periphery of said partition,
- said partition is configured to direct liquid descending onto said partition towards said flow gap, and
- a highest point of the flow gap is positioned at a lower level than a highest point of the pump inlet.

* * * * *